United States Patent [19]
Lurie et al.

[11] Patent Number: 5,645,522
[45] Date of Patent: Jul. 8, 1997

[54] DEVICES AND METHODS FOR CONTROLLED EXTERNAL CHEST COMPRESSION

[75] Inventors: Keith G. Lurie, Minneapolis, Minn.; Todd J. Cohen, Port Washington, N.Y.

[73] Assignees: The Regents of the University of California, Oakland, Calif.; AMBU International A/S, Copenhagen, Denmark

[21] Appl. No.: 58,195

[22] Filed: May 4, 1993

Related U.S. Application Data

[63] Continuation-in-part of Ser. No. 686,542, Apr. 17, 1991.
[51] Int. Cl.⁶ .................................................. A61H 31/00
[52] U.S. Cl. ............................................ 601/43; 607/142
[58] Field of Search ............................ 601/6–14, 41, 601/43, 44; 4/255.01–255.11

[56] References Cited

U.S. PATENT DOCUMENTS

| | | | |
|---|---|---|---|
| 219,428 | 9/1879 | Armstead | 4/255.11 |
| 517,481 | 4/1894 | Pressey. | |
| 728,003 | 5/1903 | Pfanschmidt et al. | |
| 1,175,671 | 3/1916 | Acklen. | |
| 1,193,476 | 8/1916 | Block | 4/255.11 |

(List continued on next page.)

FOREIGN PATENT DOCUMENTS

| | | |
|---|---|---|
| 1476518 | 4/1967 | France. |
| 468358 | 11/1928 | Germany. |
| 804025 | 4/1951 | Germany. |
| 256694 | 8/1948 | Switzerland. |
| 274306 | 7/1927 | United Kingdom. |
| 1187274 | 4/1970 | United Kingdom. |
| WO85/00018 | 1/1985 | WIPO. |

OTHER PUBLICATIONS

Krieger, Lisa M. "Toilet Plunger Successful in CPR," The San Francisco Examiner, Oct. 3 1990.

Cohen et al., "Active Compression–Decompression", *JAMA The Journal of the American Medical Association*, (3 Jun. 1992), vol. 267, No. 21, pp. 2916–2923.

Ambu International A/S, Copenhagen, DK, "Directions for Use Ambu® CardioPump™", published in Sep. 1992, pp. 1–8.

*Primary Examiner*—Richard J. Apley
*Assistant Examiner*—John Mulcahy
*Attorney, Agent, or Firm*—Townsend and Townsend and Crew LLO

[57] ABSTRACT

A device for performing active compression/decompression cardiopulmonary resuscitation includes an applicator body with an upper surface and a lower surface. The lower surface includes provisions for detachably securing to the patient's chest, such as a vacuum cup or an adhesive layer. For manual resuscitation, the upper surface will include a strap or other structure for securing a performer's hand thereto. In an exemplary device, a disc-shaped handle is attached to the upper surface of a vacuum cup applicator by a short connecting stem structure. A pressure gauge mounted to the handle permits the performer to monitor how much force is being applied in both the compression and decompression phases. For automatic applications, a mechanical drive member will be secured to the upper surface. By alternately pressing and lifting on the applicator device, the patient's chest can be compressed and expanded to improve induced ventilation and circulation.

6 Claims, 8 Drawing Sheets

U.S. PATENT DOCUMENTS

| | | | |
|---|---|---|---|
| 1,460,927 | 7/1923 | Thompson et al. | |
| 2,067,268 | 1/1937 | Hans | 601/41 |
| 2,128,217 | 8/1938 | Anderson | 4/255.02 |
| 2,204,738 | 6/1940 | Swan | |
| 2,406,317 | 8/1946 | Bonde | 4/255.11 |
| 2,742,251 | 4/1956 | Udvardy | |
| 2,879,765 | 3/1959 | Featherston | |
| 3,138,803 | 6/1964 | Caplan et al. | 4/255.01 |
| 3,228,392 | 1/1966 | Speyer | 128/55 |
| 3,534,733 | 10/1970 | Phipps et al. | |
| 3,644,943 | 2/1972 | Leonardo et al. | 4/255.11 |
| 3,783,865 | 1/1974 | Ricketts | |
| 3,958,564 | 5/1976 | Langguth | |
| 3,994,032 | 11/1976 | Spickofsky | 4/255.11 |
| 4,059,099 | 11/1977 | Davis | 128/28 |
| 4,077,400 | 3/1978 | Harrigan | |
| 4,095,590 | 6/1978 | Harrigan | |
| 4,166,458 | 9/1979 | Harrigan | |
| 4,196,722 | 4/1980 | Vanderwoude | |
| 4,198,963 | 4/1980 | Barkalow et al. | |
| 4,237,872 | 12/1980 | Harrigan | |
| 4,429,688 | 2/1984 | Duffy | |
| 4,554,910 | 11/1985 | Lally | 601/41 |
| 4,881,527 | 11/1989 | Lerman | |
| 5,114,006 | 5/1992 | Wilk | 4/255.11 X |
| 5,239,708 | 8/1993 | Irwin | 4/255.03 |
| 5,295,481 | 3/1994 | Geeham | 601/43 |

DEVICES AND METHODS FOR CONTROLLED EXTERNAL CHEST COMPRESSION

This application is a continuation-in-part of application Ser. No. 07/686,542, filed on Apr. 17, 1991, now abandoned, the full disclosure of which is incorporated herein by reference.

BACKGROUND OF THE INVENTION

1. Field of the Invention

The present invention relates generally to devices and methods for performing external chest compression as a part of cardiopulmonary resuscitation procedures. In particular, the present invention relates to the use of devices which provide for alternately compressing and actively expanding a patient's chest to induce both ventilation and blood circulation.

Sudden cardiac arrest is a major cause of death worldwide and can arise from a variety of circumstances, including heart disease and trauma such as electrical shock and suffocation. To improve a patient's chance of survival (and diminish the likelihood of brain and heart damage resulting from oxygen deprivation), it is essential that measures be taken as soon as possible to at least partially restore the patient's respiration and blood circulation. Approximately thirty years ago, techniques for external chest compression, generally referred to as cardiopulmonary resuscitation (CPR), were developed and have enjoyed great success in reducing mortality resulting from sudden cardiac arrest. Such techniques, however, have remained largely unchanged over the past two decades.

External chest compression relies on actively applying pressure to the patient's chest in order to increase intrathoracic pressure. Such pressure increase will induce blood movement from the region of the heart and lungs through the peripheral arteries, thus partially restoring the patient's circulation. Phase 1 of traditional CPR is referred to as the "active compression phase" where the chest is compressed by the direct application of external pressure. Phase 2, referred to as the "relaxation phase," occurs when pressure is withdrawn and the natural elasticity of the patient's chest wall causes expansion. While such expansion is generally sufficient to refill the cardiac chambers with some blood, it is insufficient to ventilate the patient, i.e., fill the lungs with sufficient air to oxygenate the blood. Thus, conventional CPR further requires periodic ventilation of the patient, e.g., mouth-to-mouth ventilation, in order to provide the air necessary for blood oxygenation.

Manual CPR procedures generally require performers to lean over the patient and to apply pressure using the palms of their hands to the patient's sternum as the patient lies supine on a flat surface. If no one else is available, the performer must periodically shift position to ventilate the patient through a mouth-to-mouth procedure. Such manual procedures are thus very tiring to the performer and furthermore have been found to result in only marginal circulation.

Manual CPR procedures can also result in injury to the patient. For example, pressure applied by the palm of the hand can fracture the patient's sternum and/or ribs and cause other traumatic injury, especially if the performer's hand position is inadvertently shifted laterally to an improper location on the patient's chest. The performance and safety of CPR procedures can be enhanced through the use of various mechanical and automatic machines for applying external chest compression and optionally ventilating the patient by providing supplemental oxygen or air. The machines may be as simple as a "cardiac press" which is a manually operated lever which provides a mechanical advantage in performing chest compression. More sophisticated machines can provide chest compression and/or ventilation through a variety of other mechanisms, including the use of pressurized chambers for compressing the chest cavity. While such machines can be effective, their bulk, weight, and cost limit their availability. In particular, such machines are not widely available outside of medical facilities and their size is a deterrent to providing such equipment in emergency vehicles.

CPR is often administered in conjunction with other procedures which, taken together, are referred to as advanced cardiac life support (ACLS). Most commonly, CPR is administered while the patient undergoes both electrocardiographic monitoring (ECM) and electrical defibrillation. Both ECM and defibrillation require the attachment of electrodes to the patient's chest. The need to attach electrodes can interfere with the ability to administer CPR, particularly the ability to administer manual CPR.

It would therefore be desirable to provide improved devices and methods for performing external chest compression in conjunction with CPR and ACLS procedures. It would be particularly desirable if such methods and devices provided enhanced ventilation and blood circulation in the patient undergoing treatment, preferably reducing or eliminating the need to separately ventilate the patient. Desirably, the methods and devices should be simple and easily stored so that they can be maintained in emergency vehicles, non-medical facilities, and even the home. The devices should be suitable for performing enhanced manual CPR, in particular by converting Phase 2 chest expansion from a passive event to an active process to improve venous blood return from the heart and enhance airflow into the lungs (facilitated ventilation). The devices should optionally be designed to facilitate use by a performer kneeling by the patient and using extended arms to apply upward and downward force. In particular, the devices should be designed to promote adherence to the patient's chest (during the upward stroke) and to minimize lateral displacement (during the downward stroke).

2. Description of the Background Art

Devices for performing artificial respiration by compressing and expanding a patient's abdomen are described in U.S. Pat. Nos. 2,204,738; 2,067,268; 1,175,671; and 517,481. Devices for compressing a patient's chest for external cardiac massage are described in French Patent No. 1,476,518; British Pat No. 1,187,274; and U.S. Pat. No. 4,198,963. French Patent 1,476,518, describes a vacuum cup structure and a contact pad which are disposed in a frame and drive apparatus and separately actuated to enhance cardiac massage and respiration, respectively. U.S. Pat. No. 4,881,527, describes a chamber which may be placed over a patient's chest to alternately apply pressure and vacuum to compress and expand the chest. U.S. Pat. Nos. 4,429,688 and 4,196,722, describe hand-held vacuum cups which are intended for applying percussive therapy to the lungs (chest physiotherapy). The devices are intended for repeatedly striking a patient's chest, not for applying a continuous compression and expansion. A variety of vacuum cup designs have been proposed as body massage devices. See, for example, U.S. Pat. Nos. 2,879,765; 2,742,251; 1,460,927; and 728,003, and British Patent Specification 274,306. German Patentschrift 468358 may also be pertinent. Vacuum cup electrodes for placement on humans or animals are described in U.S. Pat. Nos. 3,534,733; 3,783,865; 3,958,564; 4,077,400; 4,095,590; 4,166,458; 4,237,872; and WO 85/00018.

A device for applying pressure and vacuum to a patient's abdomen to assist in breathing was described by Dr. Rudolf Eisenmenger in Wiener Medizinische Wochenschrift, page 807, Aug. 5, 1939. The device is further described in a brochure of the Biomotor Company, Munich, Germany, undated.

Anecdotal accounts of the use of a toilet plunger for performing CPR have been reported by one of the inventors herein. See, Lurie et al. (1990), Journal of the American Medical Association, Oct. 3, 1990, page 1661; and San Francisco Examiner, article entitled "Toilet Plunger Successful in CPR," October 1990.

The use of mechanical devices for performing chest compression and CPR is described in Textbook of Advanced Cardiac Life Support, Chapter 4, American Heart Association, Second Edition, 1987.

The exemplary device of the present invention has been described in a brochure of AMBU International A/S, Copenhagen, Denmark, entitled Directions for Use of AMBU® Cardiopump™, published in September 1992.

The full disclosures of each of these references are incorporated herein by reference.

SUMMARY OF THE INVENTION

According to the present invention, devices and methods are provided for the enhanced performance of cardiopulmonary resuscitation (CPR) and advanced cardiac life support (ACLS) procedures. The devices comprise a vacuum cup, a connecting stem having a lower end attached to an upper surface or wall of the vacuum cup, and a handle attached to an upper end of the connecting stem. In a first aspect of the present invention, the vacuum cup includes a lower lip disposed in a generally horizontal contact plane and the handle includes a pair of generally parallel, transversely spaced-apart gripping surfaces located in a plane parallel to the contact plane. Such parallel spaced-apart gripping surfaces allow the performer of a cardiopulmonary resuscitation procedure to grasp opposite sides of the handle with palms facing each other and wrists aligned parallel to each other along lines which are aligned with the user's body as the user leans over the patient. Such orientation of the user's wrists and hands has been found to provide for particularly stable application of alternating downward and upward pressure strokes, as described in more detail hereinafter. In particular, it has been found that a tendency for the device to "roll" away from vertical during the downward application of force is greatly reduced. Moreover, any tendency for the device to migrate from the desired target location (i.e., the patient's sternum) is greatly diminished. Such handle designs have been found to be superior to alternative designs such as T-bar handles, hand straps, and the like.

In an exemplary embodiment of the present invention, the device handle is in the form of a circular plate or disc which defines a continuous outer periphery wherein the gripping surfaces are defined by diametrically opposed portions of the periphery. The disk-shaped handle preferably has a diameter in the range from about 15 cm to 30 cm, and will have a cross-sectional profile which facilitates gripping by a performer using extended arms with the palms of the performer's hands being pressed against the upper surface of the disk. Preferably, the handle will include a continuous peripheral flange which permits gripping by the performer's fingers while the palms of the performer's hands press down on an upper surface of the handle.

In a second aspect of the present invention, the connecting stem includes a horizontal contact surface which engages a central region of the upper wall of the vacuum cup and which compresses that region downward onto the midsternum region on the patient's chest as downward force is applied on the handle. The contact surface has an area in the range from 15 $cm^2$ to 40 $cm^2$, which has been found to provide effective chest compression while minimizing trauma to the patient. The central region of the upper wall of the vacuum cup will preferably be composed of a soft, elastomeric material and will be thickened in order to provide a cushion which further protects the patient from trauma associated with the application of compressive force.

In a third aspect of the present invention, the vacuum cup of the resuscitation device is composed of an elastomeric material and includes an upper chamber and an outwardly flared lower lip. A reinforcement ring circumscribes the vacuum cup in a generally horizontal plane above the flared lower lip, usually defining a circumferential restriction between the upper chamber and flared lower lip. The reinforcement ring is composed of a rigid material, typically being a relatively rigid plastic or metal ring, and is disposed over the outer surface of, within, or over the inner surface of the vacuum cup. The ring is thus able to inhibit deformation of the cup during use. In particular, the reinforcement ring ensures that soft skin in contact with the flared lower lip seal cannot be pulled inward by vacuum during the upward stroke (decompression) and thus distort and break the vacuum seal. Moreover, the involuted shape allows the periphery of the flared lip to lift easily and vent excess air during each compression stroke. Thus, the vacuum is renewed during each compression stroke and a very reliable grip on a wide range of chest anatomies can be achieved. Indeed, the design helps ensure that increased force applied on the upward stroke results in an enhanced vacuum within the vacuum cup.

According to the method of the present invention, the cardiopulmonary resuscitation of a patient suffering cardiac arrest and apnea is effected using devices generally as described above. The performer grasps the transversely spaced-apart parallel gripping surfaces on the device handle and positions the vacuum cup generally over the patient's sternum. The performer then presses downwardly on the handle with a sufficient force so that a lower end of the stem involutes or collapses the upper wall of the vacuum cup directly against the sternum. The force compresses the patient's chest sufficiently to induce blood circulation from the chest. The performer then pulls upwardly on the handle so that the vacuum cup (which adheres to the patient's chest by virtue of the negative pressure within the cup) actively expands the patient's chest to induce blood circulation into the chest and ventilate the patient's lungs. The downward and upward strokes are repeated at a rate sufficient to maintain blood circulation and enhance ventilation, typically with a compression distance in the range from about 3.5 cm to 5 cm and a rate in the range from 60 repetitions to 100 repetitions per minute. The device and method have been found to be most useful when the performer kneels beside the patient and grasps the handle with fully-extended arms, with the performer's palms engaging the upper surface of the handle and fingers grasped around the peripheral flange of the handle. The performer may then apply the necessary downward and upward strokes with fully-extended, locked arms while holding the device in a very stable configuration.

DESCRIPTION OF THE SPECIFIC EMBODIMENTS

According to the present invention, methods and devices are provided for performing manual and automated cardiopulmonary resuscitation (CPR), optionally in combination with electrocardiographic monitoring (ECM) and/or electrical defibrillation as part of advanced cardiac life support (ACLS) procedures. The device comprises an applicator body having an upper surface and a lower surface. The lower surface is adapted to adhere to a patient's chest during the performance of CPR so that the intrathoracic region of the chest can be both compressed by pressing on the applicator body and actively expanded by lifting upward on the applicator body.

In a particular embodiment intended for manual CPR, the upper surface of the applicator body will include a strap or other means for securing at least one hand of the person performing the CPR procedure. In this way, the performer can alternately apply active compression and active expansion by pushing and pulling with the strapped hand(s) without the need to grasp the applicator body in any way. This is a great advantage when the CPR is being performed over extended periods since the need to periodically grasp the applicator to expand the patient's chest would be very tiring to the performer. In addition, time wasted in relocating the performer's hands to the proper chest position would be reduced since the applicator would remain secured to the proper location on the chest by vacuum and/or other adhesive means.

In another specific embodiment, the upper surface of the applicator body can be attached to a mechanical drive element, such as a handle or a mechanical link which is part of a powered automatic drive system. In this way, active automatic compression and expansion of the patient's chest can be performed.

In a third and preferred specific embodiment of the present invention, the applicator is a vacuum cup (as described in more detail hereinafter) and a handle is attached to an upper surface or wall of a vacuum cup by a connecting stem. The handle preferably includes a pair of generally parallel, transversely spaced-apart gripping surfaces which permit a performer to grasp the handle with two hands, applying force with the palms of the hands and lifting up with fingers which are curled around the gripping surfaces. By "generally parallel," it is meant that the performer will be able to grasp opposite sides of the handle with the palms of the hands facing each other. In a particularly preferred design, the gripping surfaces are located in a plane which is parallel to a contact plane defined by a lower lip of the vacuum cup, i.e., the portion of the vacuum cup which contacts and adheres to the patient. In a second particularly preferred aspect, the vacuum cup includes a reinforcement ring which circumscribes the cup and divides it into a lower flared lip portion and an upper chamber portion. The reinforcement ring maintains the structural integrity of the vacuum cup during use, preventing the cup from deforming to break the vacuum seal when disposed against soft tissue.

In both manual and powered systems, the active expansion of the chest which occurs when the applicator body is lifted causes a negative pressure within the intrathoracic region, drawing air into the lungs to ventilate the patient. This is a particular advantage since it reduces or eliminates the need to otherwise ventilate the patient, such as through mouth-to-mouth resuscitation. In addition, such active expansion causes peripheral blood to move more rapidly back into the right side of the heart and lungs, resulting in increased left heart blood flow during the next compression phase.

Optionally, the applicator body will include an electrode in its lower surface which can facilitate performance of ECM and/or electrical defibrillation. The stem or other connector will then include wires or other electrical conductors for connecting the electrode(s) to external equipment in a conventional manner.

The applicator body acts as an interface element between a force-applying source, e.g., the performer's hands or the mechanical drive element, and the sternum region on the patient's chest to which the force is applied. The applicator is designed to both uniformly distribute the applied force over a predetermined area, i.e., the contact area between the applicator and the chest, as well as to provide a cushion to decrease the likelihood of injury resulting from the applied compressive force. Usually, the applicator body will be resilient to provide the desired cushion and may further have the ability to distribute the force uniformly by conforming to the contour of the patient's chest. In addition, the applicator is designed to remain fixed to the chest wall at the desired location for applying compression and expansion, thus eliminating the need to relocate the proper location each time compression is resumed, as is necessary with traditional CPR.

A variety of specific designs for the applicator body can fulfill these objectives. The applicator body can be formed as a solid pad from a resilient material, such as a natural or synthetic elastomer. Alternatively, the applicator body may be formed as an open or partially open structure, optionally containing an enclosed gas, gel, or the like, to enhance the shock absorbing and distributing capability of the body. In the case of pad-like applicator bodies, it will be necessary to provide additional means for adhering the lower surface of the body to the patient's chest. Typically, an adhesive material can be formed over all or part of the lower surface.

Suitable adhesive materials include pressure-sensitive adhesives such as those which are commonly used on medical bandages, transdermal patches, and other medical applications. The most useful adhesives will be natural and synthetic rubber based formulations, particularly polyisobutylenes. Other suitable adhesives include acrylic and silicon-base materials. When used in conjunction with electrodes, as described hereinafter, swollen hydrogels, such as poly(vinyl pyrrolidone), may find use.

The preferred embodiment of the applicator body will comprise a resilient vacuum cup having a hollow interior, where the hollow interior is placed against the patients chest so that a vacuum or "suction" is created when the applicator body is compressed thereagainst. Thus, when the vacuum cup structure is subsequently lifted according to the method of the present invention, the patient's chest will be actively expanded. The vacuum cup design is advantageous both because of its inherent adherent characteristics as well as its natural resilience which provides a cushion to protect the patient and promote the even distribution of pressure (force) over the interface region with the patient's chest. Even with the vacuum cup design, it my be desirable to provide an adhesive layer (using the materials described above) over at least a portion of the lip of the vacuum cup which contacts the patient's chest. Adhesive helps hold the vacuum cup applicator body in place and helps assure that the desired vacuum is maintained.

As an alternative to the adhesive, the vacuum cup may be designed to promote maintenance of vacuum or negative pressure within the cup to enhance adherence and reduce undesired migration of the cup across the patient's chest. Such a design may employ a lower flared lip and an upper bell-shaped chamber. The lower lip and upper chamber are joined at a transition region having a reduced diameter, and a reinforcement ring is located at or just above this reduced diameter transition region. The reinforcement ring will be composed of a rigid material, typically being rigid plastic or metal. The ring may be placed around the exterior surface of the vacuum cup, be molded within the cup, or be placed around the interior of the cup. The presence of the reinforcement ring helps assure that the vacuum cup, which is otherwise composed of an elastomeric material, will not unduly deform during use. In particular, the reinforcement ring prevents the vacuum cup from drawing up soft tissue into its interior and thus permitting an edge of the lip to raise from the tissue and break the internal vacuum.

It will frequently be desirable to form the applicator body as a laminated or layered structure, usually having one or more upper layers which are rigid relative to the lower layer(s). The relatively rigid upper layer(s) will act to receive a localized compressive force, either from the performer's hand or from a mechanical driver, and to evenly distribute the force over the lower, more resilient layers.

For manual applicator designs, means for securing at least one hand will be provided on the upper surface of the applicator body. The means for securing can be a strap, mitten, glove, or the like, which permits the performer to both press down on the applicator body and lift upward on the body without the need to grasp the applicator body in any way. The securing means should be attached to the upper surface so that the upward force applied by the performer's hand will be relatively evenly distributed over the applicator body. The use of a relatively rigid upper surface on the applicator body will help provide such even force distribution.

The dimensions of the applicator body will be chosen to provide a desired interface area between the applicator and the patient's chest. Typically, for adult patients, the applicator will have a circular periphery with a diameter in the range from about 8 to 25 cm, preferably being in the range from about 10 to 20 cm. For children, the dimensions may be as small as 3 cm. Other, non-circular geometries may also find use, and it is necessary only that the applicator body be shaped to provide for a desired force distribution over the patient's sternum as well as to provide for sufficient adherence to allow the patient's chest to be expanded when the applicator body is raised upward.

The thickness of the applicator body is not critical and will depend on the particular body design. For solid, pad-like applicator bodies, the thickness will typically be in the range from about 1 to 10 cm, more typically in the range from about 2 to 8 cm, depending on the resiliency of the material employed. For vacuum cup designs, the maximum thickness, i.e., the maximum air gap, will be in the range from about 1 to 15 cm, more usually from about 5 to 12 cm. For manual applications, it will be desirable to provide a flat upper surface so that the user can press down evenly over the surface with one or both hands in a manner similar to conventional CPR. In this way, the performer will experience the same "feel" as conventional CPR with the advantages of the present invention of patient protection and improved ventilation and circulation. In some cases, it may be desirable to shape the lower surface of the applicator body to conform to the general contours of the human chest. In addition, it may be desirable to provide a plurality of sizes of the applicator in a single kit so that a particular applicator may be selected for the individual patient. Such kits would have applicators as small as about 3 cm in diameter for children to as large as 25 cm, usually 20 cm, in diameter for adults.

It will frequently be desirable to provide one or more electrodes in the lower surface of the applicator body. The electrodes will be exposed on the surface so that they will contact the patients chest when the applicator body is in use. Usually, when employing electrodes, the lower surface of the applicator will be coated with an adhesive or other material which promotes electrical contact with the skin. For storage, the surface will be covered with a peel-away paper or plastic protective sheet.

The electrode will be internally connected to an electrical connector or plug, typically located on the side of upper surface of the applicator body. The connector or plug will be selected to allow interconnection with conventional ECM and/or electrical defibrillation equipment. Combination ECM/defibrillation equipment is commercially available from suppliers such as Hewlett-Packard Co., Palo Alto, Calif., and Physio Control, Seattle, Wash. When used with such systems, the applicator of the present invention can act as one of the two (or more) "paddle" connectors which are secured to the patient's chest for monitoring and/or defibrillation.

Figure 1:
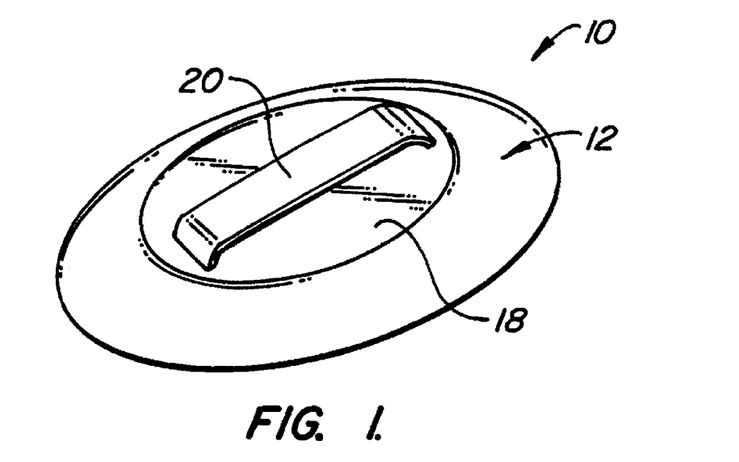
FIG. 1 is a perspective view of an applicator device constructed in accordance with the principles of the present invention.
Figure 2:
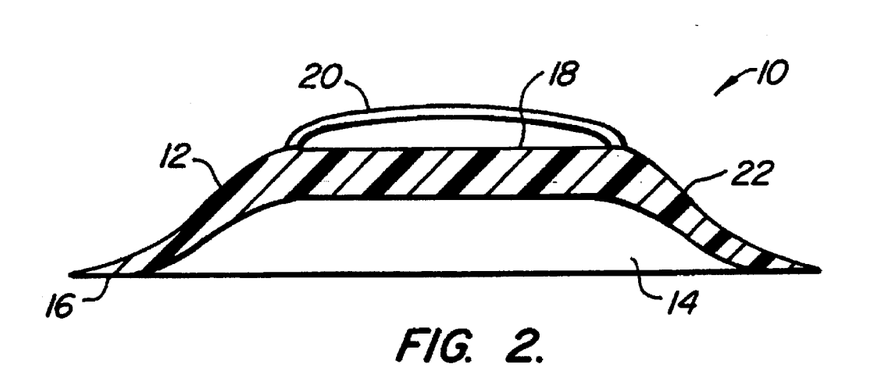
FIG. 2 is a cross-sectional view of the applicator device of FIG. 1.

Referring now to FIGS. 1 and 2, a first embodiment of the applicator device of the present invention, intended for manual CPR, is illustrated. The device 10 comprises a vacuum cup body 12 having a concave interior 14 which opens into a lower surface defined by a peripheral lip 16. The vacuum cup 12 has a substantially flat upper surface 18 having a strap 20 extending thereacross. The strap 20 is firmly secured to the upper surface so that a user can place one or both hands beneath the strap with the hand(s) being open to press directly against the upper surface.

The vacuum cup body 12 is relatively thick across its flat upper surface and tapers down to form a skirt 22 terminating at the periphery of lip 16. The thick upper surface region provides sufficient rigidity so that the applicator body 12 will not involute or "cave in" as the user presses against the upper surface. Instead, the lip 16 and skirt 22 will tend to spread outward reducing the volume of air in the concave interior 14 and providing the desired vacuum. The vacuum cup 12 will transmit sufficient force to compress the patient's chest by a desired amount, typically 3.5 to 5 cm. After the desired compression of the chest is completed, the user will lift on the applicator body 12 by raising one or both hands which in turn lift through the strap 20. The reduced pressure within the concave interior 14 will cause a vacuum or suction which acts to raise the patient's chest and actively expand the intrathoracic cavity.

Using the device 10, the performer is able to perform CPR in a manner similar to conventional manual CPR, with reduced exposure to injury since the application of force is localized to the intended region on the patient's chest with the position being "anchored" by the device itself. Additionally, the ability to actively raise the patient's chest and expand the intrathoracic cavity provides for improved ventilation and circulation of the patient.

Figure 3:
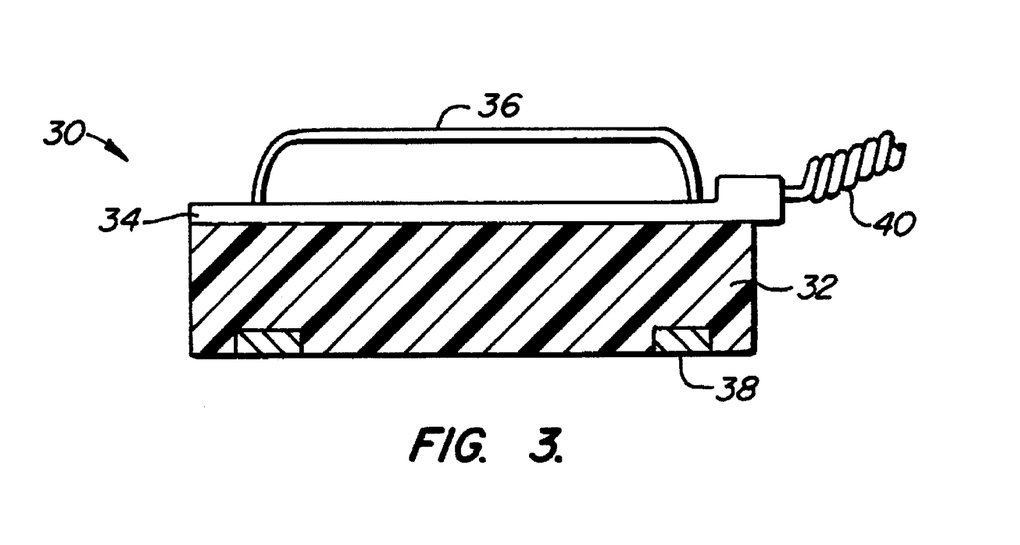
FIG. 3 is a cross-sectional view of a first alternate embodiment of an applicator device constructed in accordance with the principles of the present invention.

Referring now to FIG. 3, an alternate embodiment of a manual applicator device 30 constructed in accordance with the principles of the present invention is illustrated. The device 30 comprises a solid resilient pad structure 32 laminated to a relatively rigid upper plate 34. The resilient pad 32 can be formed from a wide variety of natural and synthetic polymers having sufficient resiliency to conform to the contours of the patient's chest while retaining sufficient compressive strength to permit the transmission of the desired force to the chest. Suitable polymers include neoprenes, low density polyethylene, soft polyvinylchloride (PVC) compounds, natural rubbers, synthetic rubbers, and the like. Suitable polymeric structure include open cell and closed cell foams. The solid pad may also comprise fluid-filled bags and structures, such as gel-filled bags and air-filled structures, which can transmit the desired force while providing desired resilience and conformity.

The upper plate 34 will be rigid relative to the resilient pad 32, typically being a rigid plastic material. A strap 36 is secured to the upper plate 34 and allows the user to place one or both hands therein in a manner similar to that described for device 10.

Applicator 30 further includes an electrode 38 which is in the form of a ring extending about the periphery of the lower surface of the pad 32. The electrode 38 will be formed from a suitable material, such as electrically conductive metals, and will be interconnected with an electrical connector cord 40 which is suitable for interconnection with an ECM system, an electrical defibrillator, or a combination ECM/defibrillator unit. Such electrode applicators will frequently be used in combination with an electrically-conductive gel, such as those commonly used with defibrillator electrodes, which can further enhance the adhesive characteristics of the applicator.

To provide the necessary adherence, the lower surface of pad 32 is covered with an adhesive which is suitable for detachably adhering to the patients chest. Suitable adhesives are described above.

Figure 4:
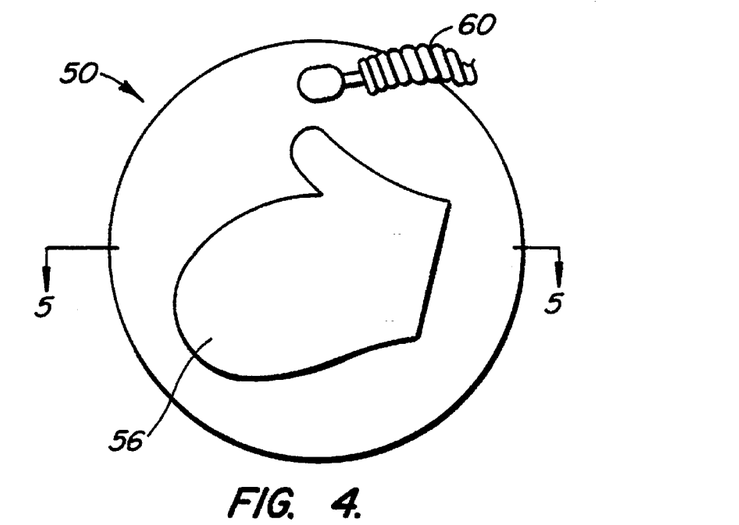
FIG. 4 is a top plan view of a second alternate embodiment of an applicator device constructed in accordance with the principles of the present invention.
Figure 5:
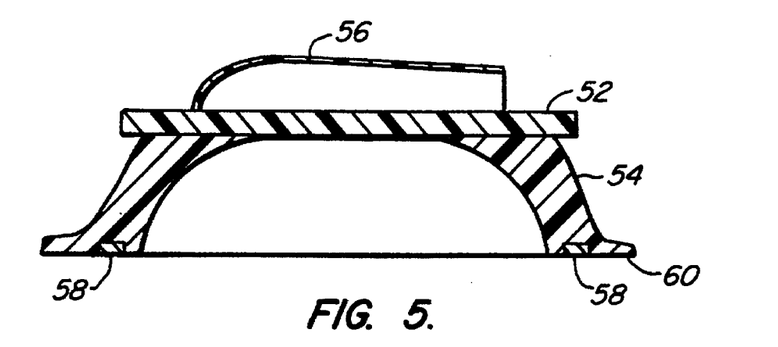
FIG. 5 is a cross-sectional view taken along line 5—5 of FIG. 4.

A second alternate embodiment 50 of the applicator device of the present invention is illustrated in FIGS. 4 and 5. The applicator device 50 includes a relatively rigid upper plate 52 and a depending vacuum cup structure 54 formed from a relatively resilient material, i.e., a material which is able to spring back. A mitten 54 is secured to the upper surface of plate 52 and is shaped to receive a performer's hand. An electrode 58 is disposed in the lip 60 of the vacuum cup 54. The electrode is interconnected to a cord 60 intended for hook-up to conventional ECM and/or defibrillation equipment.

The device 50 combines certain of the advantages of each of the previous embodiments. The use of the rigid upper plate 52 helps assure the even application of force to the patient's chest. Use of the vacuum cup structure 54 provides for an entrapped cushion of air in its concave interior, further assuring substantially uniform distribution of pressure to the patient's chest. Finally, the use of the mitten 56, rather than a strap that has previously been described, helps isolate the performer's hand from the other electrodes being used for ECM and/or defibrillation.

Figure 5A:
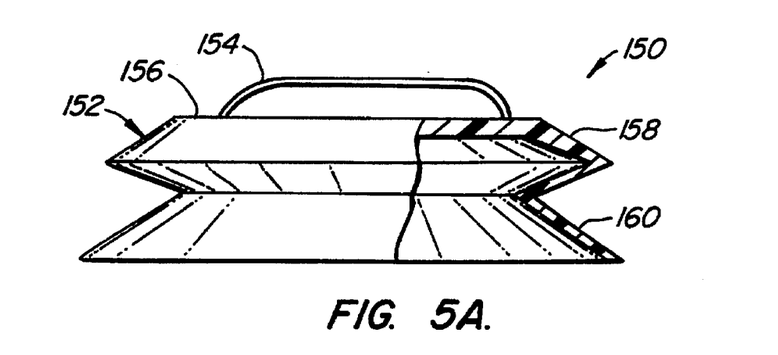
FIG. 5A is a side view of a third alternate embodiment of an applicator constructed in accordance with the principles of the present invention.

FIG. 5A illustrates an applicator 150 having a bellows or accordion configuration. In particular, applicator 150 comprises an applicator body 152 having a handle 154 secured on an upper surface 156. The applicator body 152 includes an upper pleated section 158 and a lower skirt section 160 which together define the desired bellows construction. It will be appreciated that the bellows structure may include additional pleated sections, although usually the structure illustrated will be sufficient. The applicator body 156 will usually be composed of a resilient elastic material, such as a natural rubber or synthetic rubber, and may be formed by conventional molding techniques. The applicator body 156 provides a vacuum cup which permits significant air intrusion or leakage to take place before the desired vacuum is lost.

Figure 6:
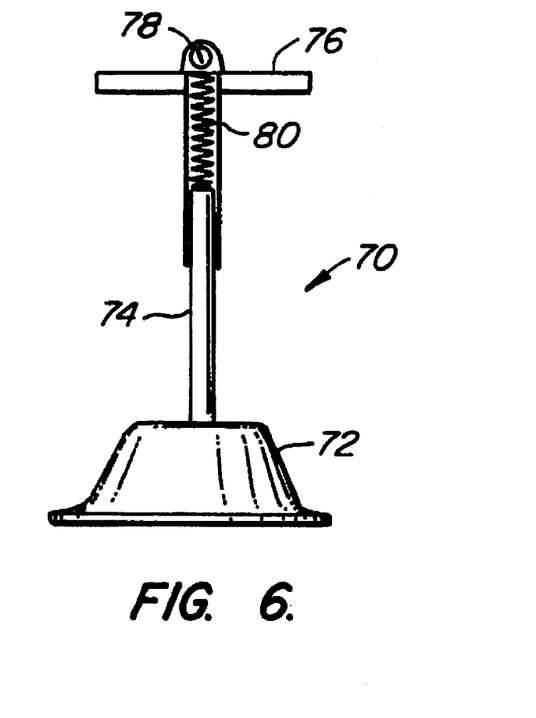
FIG. 6 is an elevational view, with portions broken away, of a third alternate embodiment of the applicator device of the present invention.

An applicator device 70 comprising an applicator body 72 and a handle 74 attached to the upper surface of the applicator body 72 is illustrated in FIG. 6. The applicator body 72 is illustrated as a vacuum cup, similar to that illustrated in FIGS. 1 and 2, but could be any of the other applicator body structures described herein. The use of an elongate handle 74 with the applicator body 72 is desirable for patient's lying on the floor or ground. A T-bar 76 on the handle 74 allows the performer to stand over the patient with one leg straddled on each side of the patient's chest, applying successive downward and upward strokes to compress and actively expand the chest.

Use of the handle interferes with the performer's ability to feel and regulate the pressure and compression being applied to the chest. For that reason, it is desirable to provide feedback information, such as a pressure gauge 78, on the handled device 70. As illustrated, the pressure gauge employs a spring 80 which is disposed between the T-bar 76 and the fixed portion of handle 74. The spring 80 also acts as a shock-absorber which helps limit excessive force applied to the patient. Other pressure measuring devices and transducers would also be suitable.

In embodiments with a handle, it may be desirable to provide a more advanced monitoring panel or readout on the handle (not illustrated) which can display a variety of patient status information and/or feedback to the person performing the CPR. Patient status information includes minute ventilation, temperature, blood pressure, heart rate, respiratory rate, and other vital signs. Such status information will often require separate monitoring devices (not illustrated) attached to the patient, and the display on the handle makes the information immediately available to the person performing the CPR. Feedback information includes pressure or force applied to the patient, depth of compression, compression rate (i.e., cycles per minute), duty cycle (i.e., portion of each cycle in which the patient is compressed), and the like. Such feedback information can be provided as discrete values, e.g., with gauges or digital readouts, or may be provided with a light or sound system which indicates when certain threshold values have been met or exceeded. It may be further desirable to provide a pacing signal, e.g., either a sound or flashing light, to facilitate maintaining a desired compression rate.

Figure 7:
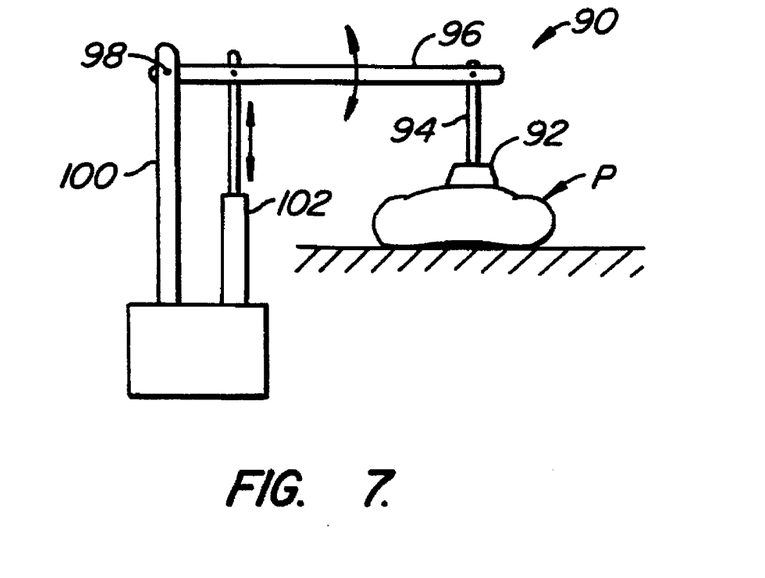
FIG. 7 is a schematic illustration of an applicator device constructed in accordance with the principles of the present invention employed in a powered actuation system.

The applicator device of the present invention may also be employed in a powered system 90 as illustrated schematically in FIG. 7. Applicator body 92 is secured to a vertical drive element 94 which is attached to a reciprocating lever arm 96. The lever arm 96 may be driven in a wide variety of ways. As illustrated, a fixed fulcrum point 98 is provided by post 100 and the lever is reciprocated up and down by a piston and cylinder 102 to provide the desired compression and expansion of the chest.

The applicator 92 is again illustrated as a vacuum cup structure, similar to that illustrated in FIGS. 1 and 2. The applicator 92 could employ any of the other applicator body structures illustrated herein, and will be particularly useful with those structures which include integral electrodes which permit ECM and defibrillation.

Figure 8:
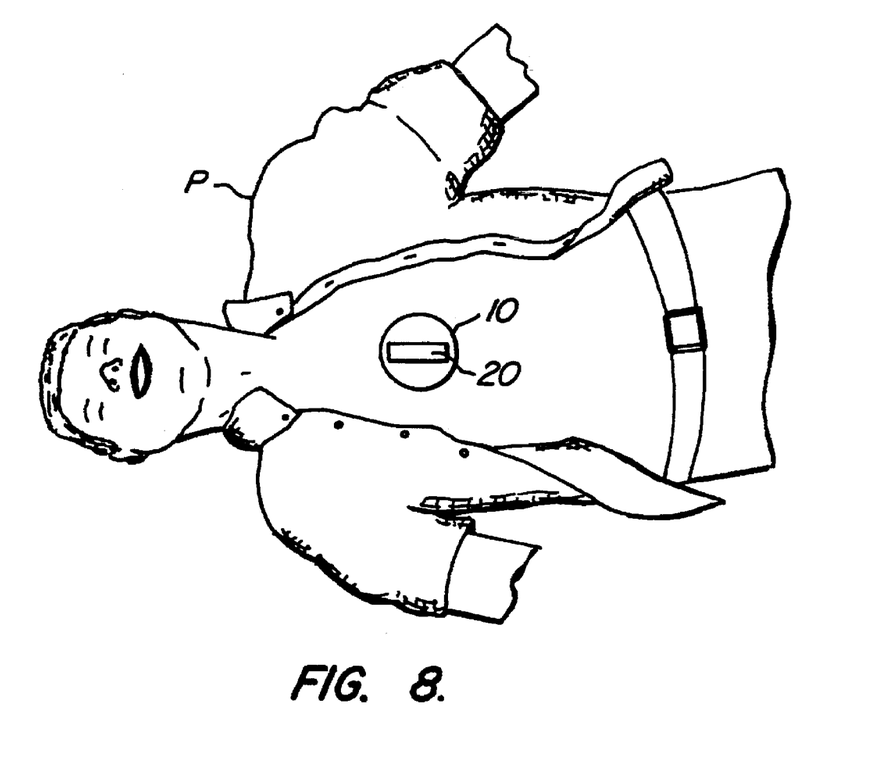
FIG. 8 illustrates the applicator device of FIG. 1 being used to perform manual cardiopulmonary resuscitation.
Figure 9:
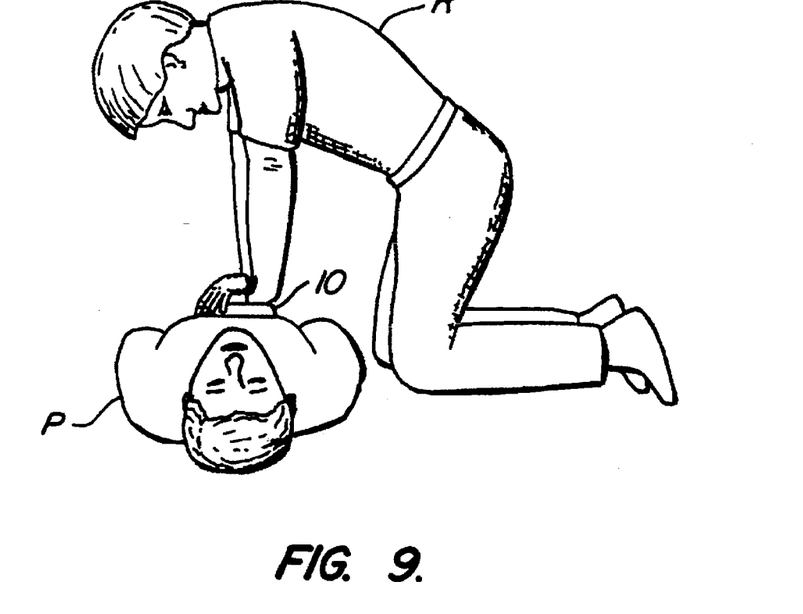
FIG. 9 illustrated the proper placement of the applicator on a patient for resuscitation as illustrated in FIG. 8.

Referring now to FIGS. 8 and 9, a method according to the present invention for applying manual CPR using the applicator device 10 is illustrated. A patient P suffering from cardiac arrest and apnea is laid on his back on a flat surface and the shirt and collar loosened to provide access to the chest. After the patient's airway is cleared in a conventional manner, e.g., by jaw thrust or neck extension, the device 10 is placed over the lower portion of the patient's sternum in the region where conventional CPR is applied (FIG. 9).

The performer then places one or both hands under the strap 20 of device 10 and begins external chest compressions at a rate of from 80 to 100 per minute. Optionally, the performer will periodically apply mouth-to-mouth resuscitation or other ventilation in order to ventilate the patient. It is an advantage of the present method, however, that the number of ventilations which must be performed is reduced.

Each chest compression should achieve a compression in the range from about 3.5 to 5 cm, and will be followed by active outward expansion of the chest by pulling up on the applicator device 10. The chest will be rapidly returned to its baseline (i.e., neither inflated nor deflated) condition until the next compression step is initiated. Typically, the compression portion of the cycle will last from about 0.2 to 0.7 seconds, while the expansion portion of the cycle will last from about 0.2 to 0.7 seconds, with the compression and expansion portions usually being equal.

The method, as described above, will be continued until heartbeat and respiration are restored or until medical support arrives.

Figure 10:
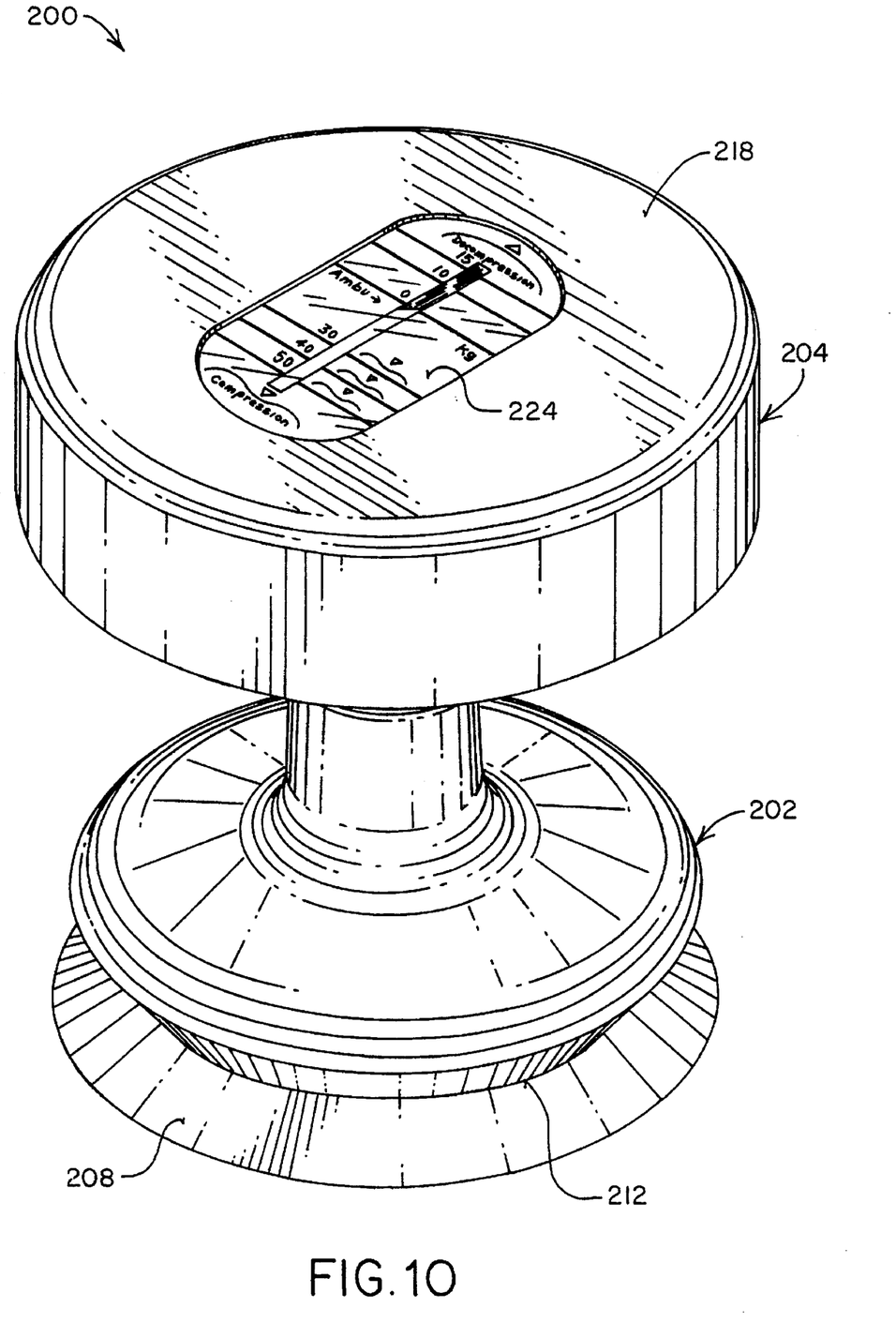
FIG. 10 is a perspective view of a preferred cardiopulmonary resuscitation device constructed in accordance with the principles of the present invention.
Figure 11:
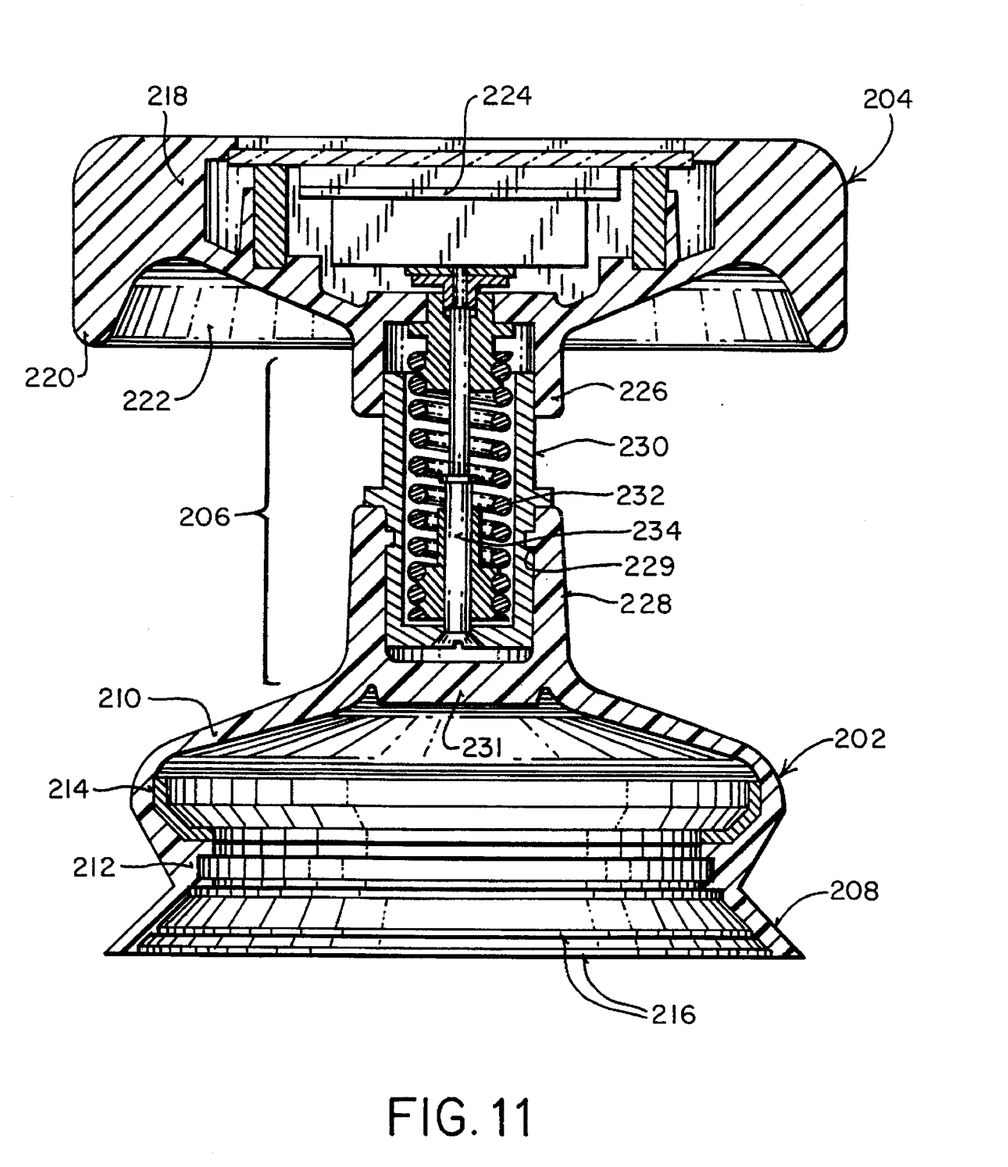
FIG. 11 is a cross-sectional view of the device of FIG. 10.

Referring now to FIGS. 10 and 11, a particularly preferred embodiment of the cardiopulmonary resuscitation device of the present invention will be described. References made in the description and the claims to "up," "upper," "upwardly," "down," "downward," "downwardly," and the like, will be made with reference to the top and bottom on FIGS. 10 and 11. These directions are consistent with the orientation of the device during normal use.

The cardiopulmonary resuscitation device 200 includes a vacuum cup 202 at its lower end, a handle structure 204, and a connecting stem structure 206 which joins the vacuum cup to the handle. The vacuum cup 202 includes a lower flared lip 208 and an upper bell-shaped chamber 210. The flared lip 208 and chamber 210 are joined at a reduced diameter juncture or transition region 212 which circumscribes the vacuum cup 202. A reinforcement ring 214 is disposed just above the juncture or hinge region 212 and acts to reinforce the shape of the upper chamber 210 and to prevent collapse of the vacuum cup 202 during use. It will be appreciated that the lower flared lip 208 is highly flexible, and the entire vacuum cup 202 is preferably formed from a soft, elastomeric material, such as silicone rubber. The lip 208 will thus be able to conform to a wide variety of patient anatomies. As upward and downward forces are applied on the resuscitation device 200, however, there will be a tendency for the vacuum cup 202 to deform and permit the vacuum within the cup to be broken during the upward, decompression stroke on the patient. The presence of the reinforcement ring 214, particularly in combination with the reduced diameter transition region 212, prevents such deformation and promotes strong adherence of the cup to the patient during the upward expansion stroke. The vacuum cup 202 further includes a pair of sealing ridges 216 formed on the interior surface of lip 208 which further promote maintenance of the vacuum seal of the cup to a patient's chest. In particular, the sealing ridges 216 help provide a good vacuum seal even on very hairy chests.

The handle 204 comprises a disc structure 218, which is illustrated as a unitary body, but will frequently be manufactured in two or more pieces to facilitate assembly. The disc structure 218 is molded or otherwise formed to define a peripheral flange 220 which defines a recessed region 222 which extends annularly around the lower face of the disc 218. Optionally, the handle 204 will have a cushioned or padded upper surface for the comfort of the performer. The combination of the flange 220 and recessed region 222 permits the performer to grasp the handle 204 by curling the fingers of each hand around the flange and into the recess and placing the palms of the hands against the upper surface. The hands will preferably be located on diametrically opposed portions of the perimeter of the handle 204. By so grasping the handle 204 with fully extended arms, a performer can maintain the resuscitation device 200 in a highly stable manner during use. That is, there will be a minimum tendency for the performer to lose control of the device 200 and for the device to roll over out of vertical alignment or to migrate out of position on the patient's sternum.

In a preferred construction, a pressure gauge 224 is mounted in the central region of the upper surface of handle structure 204. Conveniently, the pressure gauge 224 provides a positive and negative force scale which permits the user to monitor how much force is being applied in both an upward and downward direction. As illustrated, the downward scale reads from 0 (i.e., no upward or downward force being applied) to 50 kg, while the upward force scale reads from 0 to 15 kg. The device may also include printed constructions for use on the handle, such as about the handle periphery.

The connecting stem structure 206 includes both a flange 226 on the lower surface of the handle 204 and a flange 228 on the upper surface or wall of the vacuum cup 202. A stem cylinder 230 is received in the flange 228 on the vacuum cup 202, with its opposite end slidably received in the flange 226 on handle 204. The vacuum cup 202 will be detachably mounted on the stem cylinder 230, usually with the flange 228 having a ridge 229 received in an annular channel in the stem to permit replacement of the vacuum cup after use. A spring 232 is connected to and extends between both the vacuum cup 202 and handle 204, and it will be appreciated that the handle 204 may thus move upward and downward relatively to the vacuum cup 202 during use. A connecting rod 234 also extends between the vacuum cup 202 and handle 204 and, together with the spring 232, forms part of the pressure gauge mechanism 224.

Figure 12:
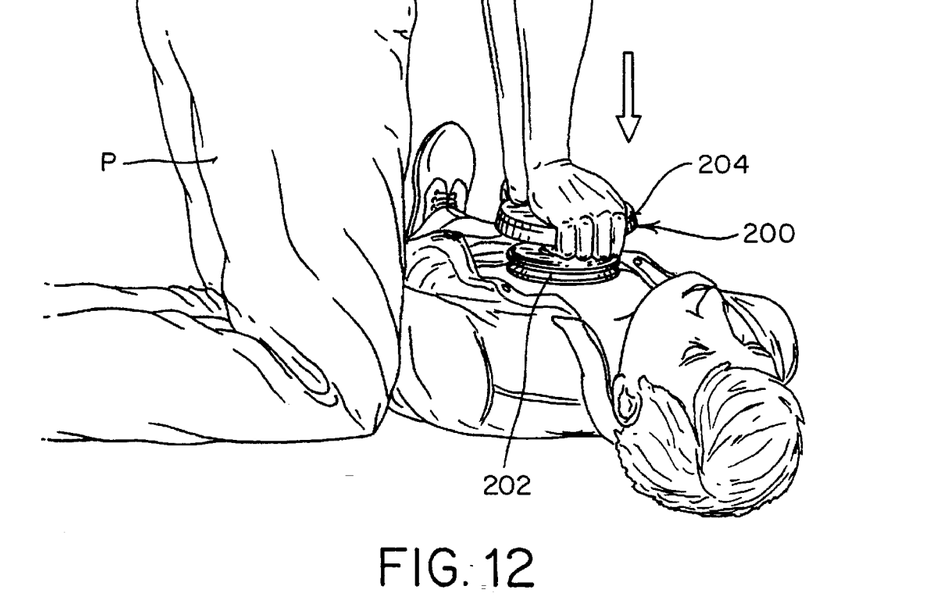
FIGS. 12 and 13 illustrate use of the device of FIGS. 10 and 11 by a performer kneeling by a patient, where the performer is using fully-extended arms and applying force through the palms of the performer's hands.
Figure 13:
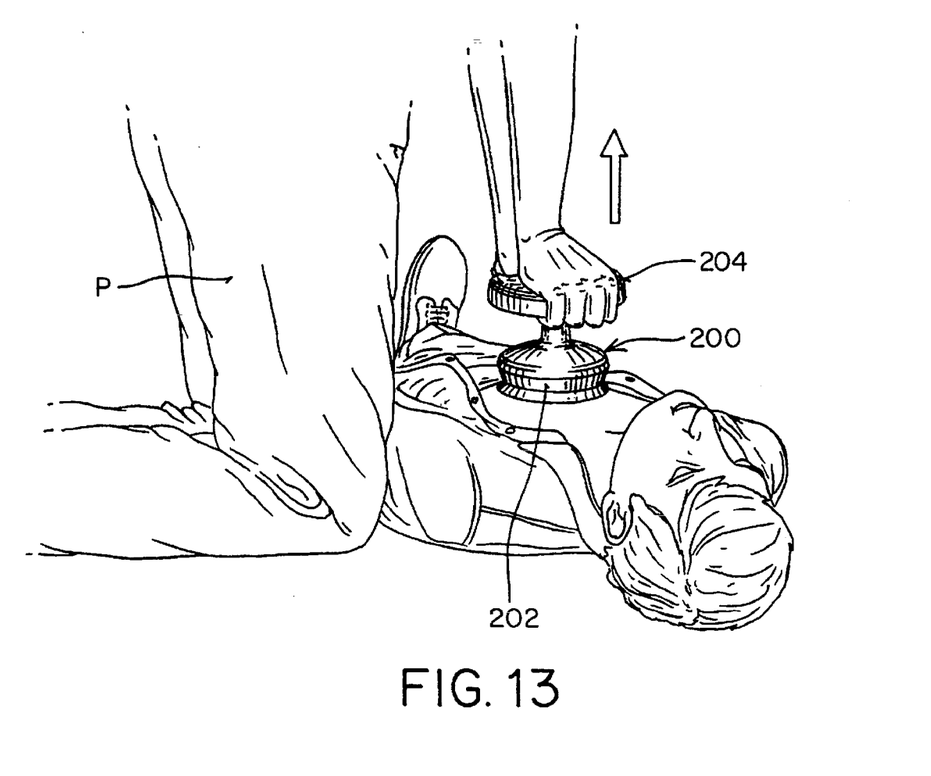

Referring now to FIGS. 12 and 13, the resuscitation device 200 is used as follows. A performer P grasps the handle 204 in both hands, pressing the palms of the hands against the upper surface while grasping the peripheral flange 220 with the fingers. The performer P locates the vacuum cup 202 on the patient's sternum and begins the procedure by pressing downwardly, typically using a force in the range from about 30 kg to 50 kg, depending on the stiffness of the chest. Sufficient pressure should be used to obtain the desired chest compression depth of about 38 mm to 51 mm.

After the compression stroke is completed, the performer P will raise the resuscitation device 200, typically using a rocking motion relying on the muscles in the thighs to raise the device. The device 200 will be raised in an amount sufficient to apply an expansion force in the range from about 10 kg to 15 kg. The compression and expansion steps will be alternated at a rate in the range from about 80 to 100 per minute.

Figure 14:
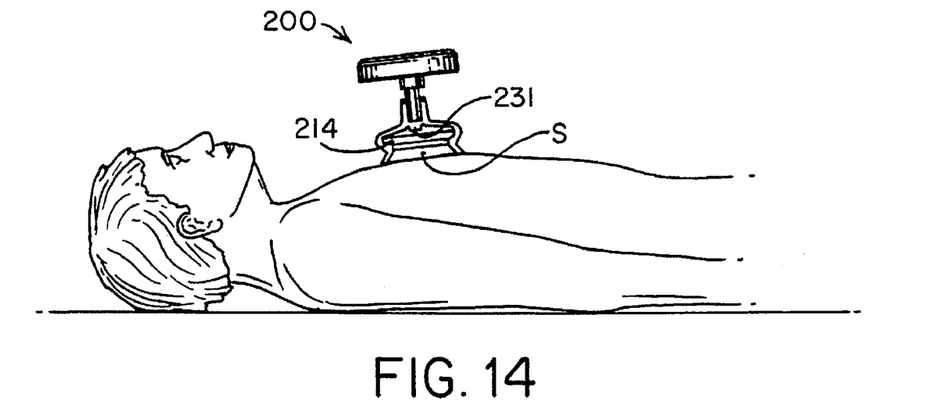
FIGS. 14–16 are schematic illustrations illustrating the internal configuration of the cardiopulmonary resuscitation device of FIGS. 10 and 11 during the positioning, compression, and active decompression steps of the method of the present invention, respectively.
Figure 15:
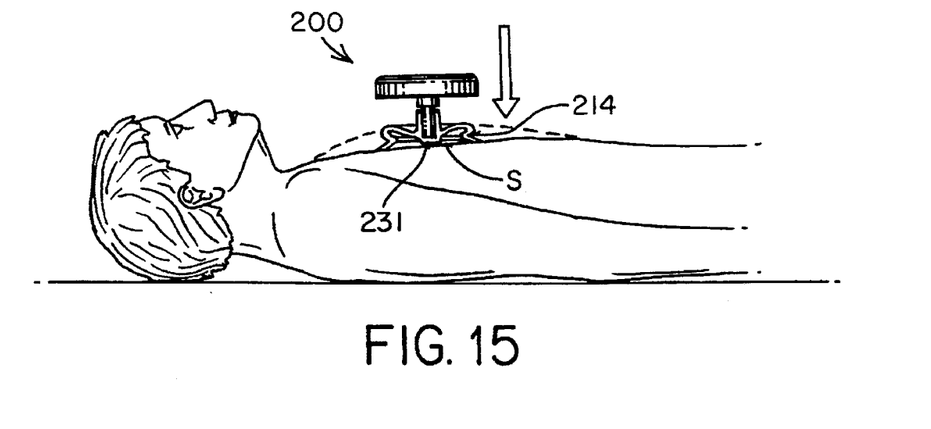
Figure 16:
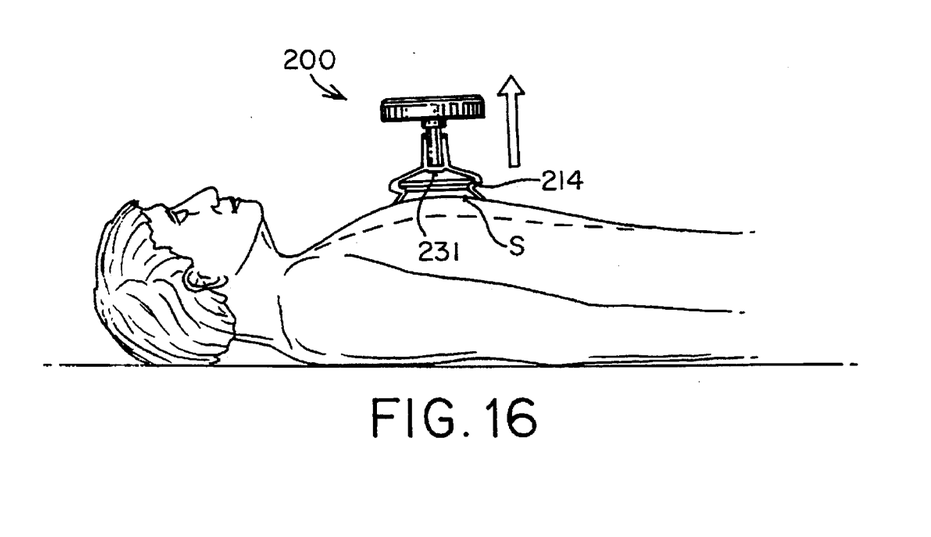

Referring now to FIGS. 14–16, use of the device 200 in resuscitating a patient will be further described. The device is initially placed in patient's mid-sternum S, as illustrated in FIG. 14. The performer P then applies sufficient downward force on the handle of device 200 so that the chest is compressed, typically by a distance in the range from 38 mm to 51 mm, as illustrated in FIG. 15. In particular, a contact pad 231 (which is preferably formed in the upper surface of the vacuum cup 202 and which is directly engaged by the lower end of the stem structure 206) of device 200 is lowered to engage the sternum S with the preferred contact area in the range from about 6 cm² to 40 cm². The contact pad 231 will be formed of a resilient material, typically silicone rubber, and softens the application of downward force through the stem structure 206. The initial position of the patient's chest is illustrated in broken line in FIG. 15. During the compression stroke, the internal volume of the vacuum cup of device 200 is reduced by collapsing the upper surface down, as illustrated in FIG. 15. The flared lower lip of device 200 allows air to readily escape during the compression stroke.

After the compression stroke is completed, the performer P immediately raises on the handle 204 of device 200 to expand the chest, as illustrated in FIG. 16. Again, the rest position of the chest is illustrated in broken line. During the chest expansion stroke, the vacuum or negative pressure will be created within the interior volume of the vacuum cup 202. Such negative pressure will cause adherence of the device 200 to the chest to permit the desired expansion. The presence of the reinforcement ring 214 will help prevent significant deformation of the vacuum cup which might permit loss of vacuum which is required for performance of the procedure. The particular design of the vacuum cup 202, including the upper chamber 214, lower flared lip 208, and reinforcement ring 214, is particularly desirable since it allows for the vacuum within the vacuum cup to be renewed on each compression stroke. In this way, use of the device is highly reliable with any tendency for the device to lose vacuum or to migrate across the patient's chest greatly reduced.

Although the foregoing invention has been described in detail for purposes of clarity of understanding, it will be obvious that certain modifications may be practiced within the scope of the appended claims.

What is claimed is:

1. A device for performing cardiopulmonary resuscitation of a patient, said device comprising:

an applicator body having an upper surface and a lower surface;

a handle secured to and extending upwardly from the upper surface of the applicator;

means on the applicator body for adhering the lower surface to the patient's chest, whereby the performer can alternately compress and actively expand the patient's chest by pressing and pulling on the applicator using the handle; and a pressure gauge on the handle, said pressure gauge measuring compression force applied by the applicator.

2. A device as in claim 1, wherein the means for adhering the lower surface to the patient's chest comprises a hollow interior in the applicator body, said hollow interior being open to the lower surface and the body being sufficiently flexible to allow the body to act as a vacuum cup.

3. A device for performing cardiopulmonary resuscitation of a patient, said device comprising:

a flexible cup having an open hollow interior a lower lip formed about the open interior;

a handle secured to and extending upwardly from the flexible cup, and a pressure gauge on the handle, said pressure gauge measuring compression force applied by the vacuum cup.

4. A device for performing cardiopulmonary resuscitation of a patient, said device comprising a flexible cup having a hollow interior and a lower lip formed about the open interior;

a handle secured to and extending upwardly from the flexible cup, said handle having means for manually grasping spaced-upwardly from the flexible cup;

an axially compressible spring in the handle, wherein said spring acts as a shock absorber between the handle and the flexible cup; and a gauge on the handle which measures compression of the handle as the device is pressed against the patient's chest.

5. A device as in claim 4, wherein the axially compressible spring comprises part of the gauge.

6. A device as in claim 5, wherein the handle has a telescoped structure with the spring therein.

* * * * *